United States Patent
Davies et al.

(10) Patent No.: US 6,740,753 B2
(45) Date of Patent: May 25, 2004

(54) OLANZAPINE CRYSTAL MODIFICATION

(75) Inventors: Julian Davies, Sylvania, OH (US); James Edward Gano, Fort Collins, CO (US)

(73) Assignee: Geneva Pharmaceuticals, Inc., Broomfield, CO (US)

( * ) Notice: Subject to any disclaimer, the term of this patent is extended or adjusted under 35 U.S.C. 154(b) by 272 days.

(21) Appl. No.: 10/024,934

(22) Filed: Dec. 19, 2001

(65) Prior Publication Data

US 2002/0086993 A1 Jul. 4, 2002

Related U.S. Application Data

(60) Provisional application No. 60/259,621, filed on Jan. 4, 2001.

(51) Int. Cl.$^7$ .............................................. C07D 495/04
(52) U.S. Cl. ....................................................... 540/557
(58) Field of Search .......................................... 540/557

(56) References Cited

U.S. PATENT DOCUMENTS

| 5,229,382 A | 7/1993 | Chakrabarti et al. | 514/220 |
| 5,631,250 A | 5/1997 | Bunnell et al. | 514/220 |
| 5,736,541 A | 4/1998 | Bunnell et al. | 514/220 |
| 6,020,487 A | 2/2000 | Bunnell et al. | 540/557 |

FOREIGN PATENT DOCUMENTS

| EP | 733 367 | 9/1996 |
| EP | 0 733 635 A1 | 9/1996 |
| EP | 830 858 | 3/1998 |
| EP | 831 097 | 3/1998 |

*Primary Examiner*—Brenda Coleman
(74) *Attorney, Agent, or Firm*—Gabriel Lopez; Diane E. Furman

(57) ABSTRACT

A novel crystal form the pharmaceutical compound olanzapine, processes for its preparation and its pharmaceutical use are disclosed.

18 Claims, 2 Drawing Sheets

OLANZAPINE CRYSTAL MODIFICATION

This application claims the benefit of Provisional Application No. 60/259,621 filed Jan. 4, 2001, the contents of which are incorporated herein by reference.

SUMMARY

This invention relates to a novel crystal form of the pharmaceutical compound olanzapine, a process for its preparation and pharmaceutical formulations thereof.

BACKGROUND

The compound 2-methyl-4-(4-methyl-1-piperazinyl)-10H-thieno{2,3-b}{1,5}benzodiazepine been named according to the U.S.A.N. as olanzapine. It is known as an anti-psychotic agent. The present invention relates to a novel olanzapine crystal modification, hereinafter designated as Form X, which is distinguished from previously known crystal forms by physical and spectroscopic properties such as melting point and powder x-ray diffraction pattern.

DETAILED DESCRIPTION

The Form X crystal modification of olanzapine has a characteristic melting point in the range from about 187° C. to about 191° C., more specifically about 187° C. to 190° C., or 189° C. to 190° C.

Figure 1:
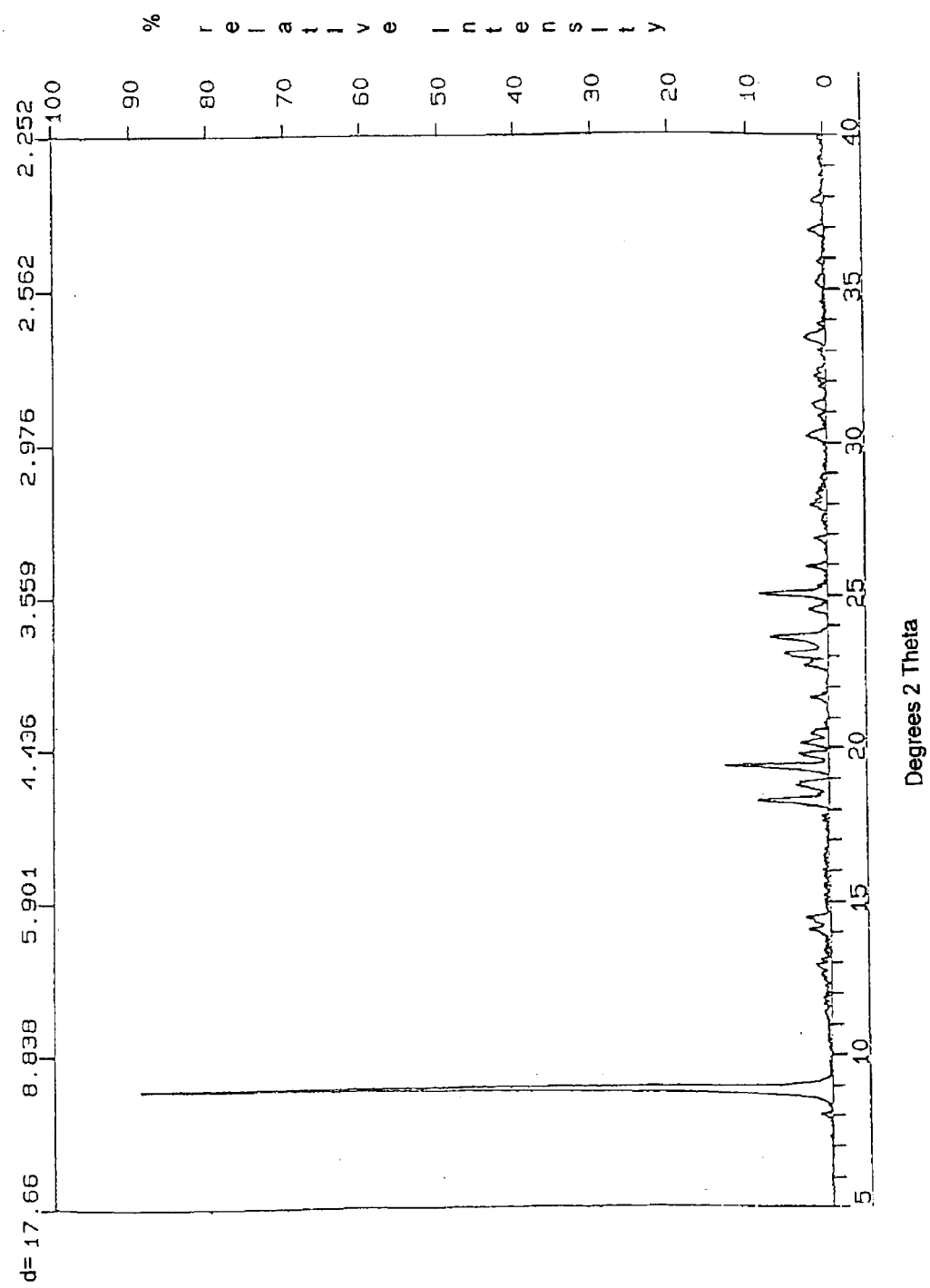
FIGS. 1 and 2 show the powder x-ray diffraction pattern of the Form X crystal modification of olanzapine obtained from Examples 1 and 2, respectively.

FIG. 1 is the powder x-ray diffraction pattern of the Form X crystal modification of olanzapine. The powder x-ray diffraction pattern of Form X olanzapine is characterized by peaks at about 11.05, 9.98, 6.24, 6.13, 3.75, 3.61, 3.53, 3.43 and 2.67 d-spacing units. Preferably, the powder x-ray diffraction pattern of Form X olanzapine is characterized by peaks at about 11.05, 9.98, 6.24, 6.13, 4.83, 4.71, 4.57, 4.48, 4.39, 4.32, 3.84, 3.75, 3.61, 3.53, 3.43, 2.95, 2.86, 2.67, 2.43 and 2.36 d-spacing units.

Thus, Form X olanzapine of the present invention is characterized by a melting point in the range from 187° C. to 191° C. and further characterized by a powder x-ray diffraction pattern having peaks at about 11.05, 9.98, 6.24, 6.13, 3.75, 3.61, 3.53, 3.43 and 2.67 d-spacing units. Specifically, Form X olanzapine is characterized by a powder x-ray diffraction pattern having peaks at about 11.05, 9.98, 6.24, 6.13, 3.75, 3.61, 3.53, 3.43 and 2.67 d-spacing units and a melting point in the range from 187° C. to 190° C., preferably 189° C. to 190° C. More specifically, Form X olanzapine is characterized by a powder x-ray diffraction pattern having peaks at about 11.05, 9.98, 6.24, 6.13, 4.83, 4.71, 4.57, 4.48, 4.39, 4.32, 3.84, 3.75, 3.61, 3.53, 3.43, 2.95, 2.86, 2.67, 2.43 and 2.36 d-spacing units and a melting point in the range from about 187° C. to about 191° C., preferably 187° C. to 190° C. or 189° C. to 190° C.

In a specific embodiment, Form X olanzapine is further characterized by the absence of powder x-ray diffraction peaks at about 10.2 to 10.3 d-spacing units, or by the absence of powder x-ray diffraction peaks in the range from 8.0 to 8.9 d-spacing units, or by the absence of powder x-ray diffraction peaks at 4.98 or 4.94 d-spacing units; especially by the absence of all of the above-indicated x-ray diffraction peaks. When such peaks are present, Form X olanzapine is identified solely by its characteristic melting point range and/or by the presence of a small peak at about 11.05 d-spacing units.

All peak values reported are truncated to 2 decimal places from the instrument report without regard to significant figures. Variances in the d-spacing values reported for any x-ray diffraction peak within ±1% are considered insignificant. The use of the expression "about" when describing the position of an powder x-ray diffraction peak is intended to provide a basis for including such insignificant variances within the characterization of the Form X crystal modification.

Preferably, the Form X crystal modification of olanzapine is in substantially pure form—substantially pure Form X being intended to mean that at least 80% by weight of the crystalline olanzapine in the sample is present as Form X. Most preferably, the Form X crystal modification is in pure form meaning that at least 90% of the crystalline Olanzapine in the sample is present as Form X. The present invention also relates to highly pure Form X crystal modification meaning that the material is essentially homogeneous Form X crystal modification.

The Form X crystal modification of olanzapine is prepared by standard crystallization techniques from an aqueous solution of a water-miscible polar organic solvent. Preferably, the Form X crystal modification is crystallized from an aqueous crystallization solution of a water-miscible lower ketone, for example an aliphatic ketone having the formula $C_1$-$C_3$—C(O)—$C_1$-$C_3$ (wherein the appropriate number of hydrogen atoms is understood). Preferred ketones are acetone and methyl ethyl ketone. In general, the aqueous crystallization solution contains the ketone and water in a ratio of from about 4:1 to about 1:1, preferably a ratio of about 2:1. Depending on the crystallization conditions, the resulting product can be a mixture of crystal forms which includes Form X olanzapine or highly pure Form X olanzapine.

Advantageously, no additional co-solvent or additional organic material is present in the aqueous crystallization solution. However, minor amounts of such co-solvents or additional organic materials are not known to cause any significant disadvantage.

The Form X crystal modification of olanzapine is used, in particular, for the preparation of pharmaceutical compositions of olanzapine. Thus, the present invention further relates to a pharmaceutical composition which comprises a pharmaceutically effective amount of the Form X crystal modification of olanzapine. Preferably, the pharmaceutically effective amount is the amount required to deliver 5 to 20 mg/day. The recommended dose is about 10 mg/day.

The following examples are intended to illustrate, but not limit, the invention.

All melting points are measured on a UNIMELT Thomas Hoover Capillary Melting Point Apparatus in an open capillary tube. The reported melting points are uncorrected unless otherwise noted.

All powder x-ray diffraction patterns are measured on a SCINTAG XDS2000 diffractometer with Cu radiaton and a solid state Ge detector cooled by liquid nitrogen at 45 kV, 40 mA, divergent slits 2 mm and 4 mm, receiving slits 1.0 and 0.2 mm, $2\theta = 3$–$70°$ continuous scan in $\theta{:}\theta$ mode. The raw intensity data are stripped of $K\alpha 2$, the background subtracted and the data smoothed using fast Fourier filtering. The samples are ground into fine powders before analysis.

EXAMPLE 1

A 0.2053 g sample of olanzapine is placed in a clean Erlenmeyer flask and a 2:1 acetone:water solution is added in 10 mL increments with stirring until the sample is dissolved. The flask is covered with cotton and the solvent is allowed to evaporate at room temperature until about 5 mL of solution remains. Upon filtration, 0.0529 g of a crystalline precipitate (25% yield) composed of small, yellow crystals is obtained. The precipitate is protected from dust with a filter paper cover and allowed to air dry on a laboratory bench for about 48 hours under ambient conditions. The dried sample is stored in a glass vial with a plastic cap.

The resulting Form X olanzapine has a melting point of 189° C. to 190° C. and shows the powder x-ray diffraction pattern depicted in FIG. 1.

EXAMPLE 2

A 0.2085 g sample of olanzapine is placed in a clean Erlenmeyer flask and 2:1 methyl ethyl ketone:water solution is added in 10 mL increments with stirring until the sample is dissolved. The flask is covered with cotton and the solvent is allowed to evaporate at room temperature until about 5 mL of solution remains. Upon filtration, 0.1055 g of a crystalline precipitate (51% yield) composed of medium-size, orange crystals is obtained. The precipitate is protected from dust with a filter paper cover and allowed to air dry on a laboratory bench for about 48 hours under ambient conditions. The dried sample is stored in a glass vial with a plastic cap.

Figure 2:
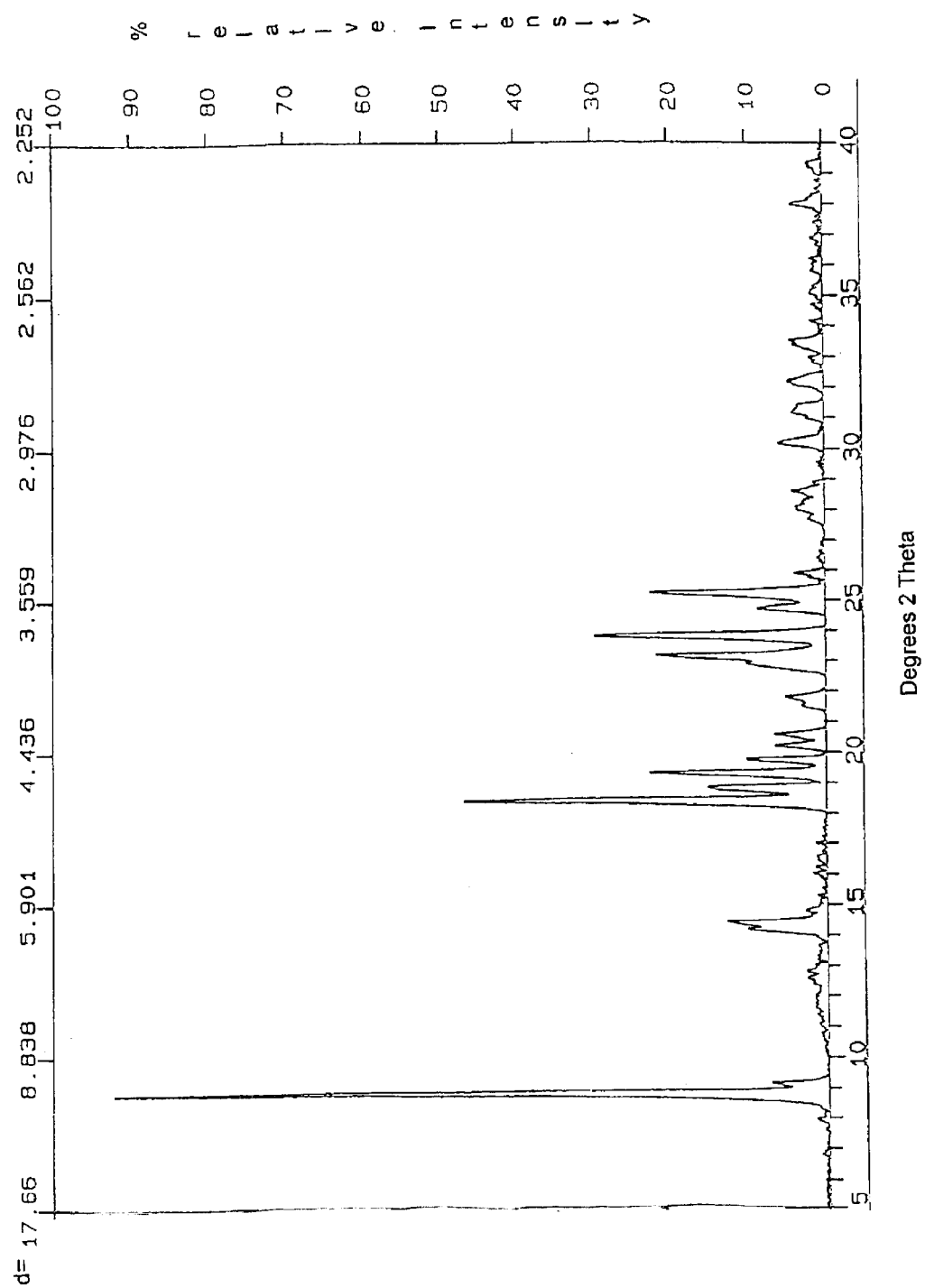

The resulting Form X olanzapine has a melting point of 189° C. to 190° C. and shows the powder x-ray diffraction pattern depicted in FIG. 2.

We claim:

1. Form X olanzapine characterized by a melting point in the range from 187° C. to 191° C.

2. Form X olanzapine characterized by a small peak at about 11.05 d-spacing units in its powder x-ray diffraction pattern.

3. Form X olanzapine of claim 1 having a powder x-ray diffraction pattern with characteristic peaks at about 11.05, 9.98, 6.24, 6.13, 3.75, 3.61, 3.53, 3.43 and 2.67 d-spacing units.

4. Form X olanzapine of claim 3 having a melting point of 187° C. to 190° C.

5. Form X olanzapine of claim 4 having a melting point range of 189° C. to 190° C.

6. Form X olanzapine of claim 5 having a powder x-ray diffraction pattern with characteristic peaks at about 11.05, 9.98, 6.24, 6.13, 3.75, 3.61, 3.53, 3.43 and 2.67 d-spacing units.

7. Form X olanzapine of claim 4 having a powder x-ray diffraction pattern with characteristic peaks at about 11.05, 9.98, 6.24, 6.13, 4.83, 4.71, 4.57, 4.48, 4.39, 4.32, 3.84, 3.75, 3.61, 3.53, 3.43, 2.95, 2.86, 2.67, 2.43 and 2.36 d-spacing units.

8. Form X olanzapine of claim 5 having a powder x-ray diffraction pattern with characteristic peaks at about 11.05, 9.98, 6.24, 6.13, 4.83, 4.71, 4.57, 4.48, 4.39, 4.32, 3.84, 3.75, 3.61, 3.53, 3.43, 2.95, 2.86, 2.67, 2.43 and 2.36 d-spacing units.

9. Form X olanzapine of claim 4 further characterized by the absence of powder x-ray diffraction peaks at about 10.2 to 10.3 d-spacing units.

10. Form X olanzapine of claim 4 further characterized by the absence of powder x-ray diffraction peaks in the range from 8.0 to 8.9.

11. Form X olanzapine of claim 4 further characterized by the absence of powder x-ray diffraction peaks at 4.98 or 4.94 d-spacing units.

12. Form X olanzapine of claim 4 further characterized by the absence of powder x-ray diffraction peaks at about 10.2 to 10.3, in the range from 8.0 to 8.9, or at 4.98 or 4.94 d-spacing units.

13. Form X olanzapine of claim 2 having a melting point range of 189° C. to 190° C.

14. A process for preparing crystalline olanzapine which comprises crystallizing olanzapine from an aqueous crystallization solution of a lower aliphatic ketone of the formula $C_1$–$C_3$—$C(O)$—$C_1$–$C_3$.

15. A process of claim 14 wherein the lower aliphatic ketone is acetone or methyl ethyl ketone.

16. A process of claim 15 wherein the aqueous crystallization solution contains the lower aliphatic ketone and water in a ratio of from about 4:1 to about 1:1.

17. A process of claim 16 wherein the ratio is about 2:1.

18. A process of claim 14 wherein the crystalline olanzapine is Form X olanzapine.

* * * * *